United States Patent [19]

Sanderson et al.

[11] Patent Number: 5,072,050
[45] Date of Patent: Dec. 10, 1991

[54] KETONE-TERMINATED POLYOXYALKYLENE COMPOUNDS

[75] Inventors: John R. Sanderson, Leander; Edward T. Marquis; John M. Larkin, both of Austin, all of Tex.

[73] Assignee: Texaco Chemical Company, White Plains, N.Y.

[21] Appl. No.: 594,464

[22] Filed: Oct. 9, 1990

[51] Int. Cl.$^5$ .............................. C07C 49/175
[52] U.S. Cl. ................................. 568/314; 568/313
[58] Field of Search ........................... 568/314, 313

[56] References Cited

U.S. PATENT DOCUMENTS

| | | | |
|---|---|---|---|
| 3,665,041 | 5/1972 | Sianesi et al. | 568/413 |
| 3,847,978 | 11/1974 | Sianesi et al. | 568/413 |
| 4,141,919 | 2/1979 | Gremmelmaier | 260/594 |
| 4,647,413 | 3/1987 | Savu | 568/413 |
| 4,980,514 | 12/1990 | Sanderson et al. | 568/405 |

OTHER PUBLICATIONS

P. L. Anelli et al., "Fast and Selective Oxidation of Primary Alcohols to Aldehydes or to Carboxylic Acids and of Secondary Alcohols to Ketones Mediated by Oxoammonium Salts Under Two-Phase Conditions", *J. Org. Chem.*, vol. 52, 1987, pp. 2559–2562.

G. Barak et al., "Selective Oxidation of Alcohols by a $H_2O_2$-$RuCl_3$ System Under Phase-Transfer Conditions", *J. Org. Chem.*, vol. 43, 1988, pp. 3553–3555.

T. Nishiguchi et al., "Oxidation of Alcohols by Metallic Nitrates Supported on Silica Gel", *J. Org. Chem.*, vol. 54, 1989, pp. 1531–1535.

*Primary Examiner*—James H. Reamer
*Attorney, Agent, or Firm*—Jack H. Park; Kenneth R. Priem; David L. Mossman

[57] ABSTRACT

Mono-, di- and tri-ketones of polyoxyalkylene compounds prepared by a method whereby the terminal hydroxyl groups of polyoxyalkylene compounds are oxidized to ketone groups with an alkali metal or an alkaline earth metal hypochlorite oxidant in the presence of acetic acid are disclosed. These compounds are useful for preparing surface active agents or they may be reacted with amines to provide fuel additives.

14 Claims, No Drawings

KETONE-TERMINATED POLYOXYALKYLENE COMPOUNDS

CROSS REFERENCE TO RELATED APPLICATIONS

This application is related to U.S. patent application for Bisulfite Addition Products of Ketone-Terminated Polyoxyalkylene Compounds of George P. Speranza and John R. Sanderson, attorneys' docket number for which is 80,955 filed of even date.

BACKGROUND OF THE INVENTION

1. Field of the Invention

This invention relates to ketone-terminated polyoxyalkylene compounds. More particularly, this invention relates to monoketone, diketone and triketone derivatives prepared by a method whereby the terminal hydroxyl groups of polyoxyalkylene compounds are oxidized to ketone groups with a hypochlorite oxidant in the presence of concentrated acetic acid. The ketone-terminated derivatives are useful as intermediates for the preparation of a wide variety of products. For example, they may be reacted with amines to provide fuel additives or converted to carboxylic acids to provide surfactants or the ketone products of this invention may be reacted with an alkali metal bisulfite to form products with good surface active properties.

2. Prior Art

It is known to react secondary alcohols and primary benzyl and allyl alcohols to the corresponding ketones and aldehydes in the presence of an oxidant such as Cu(NO$_3$)$_2$ or Zn(NO$_3$)$_2$ supported on silica gel in the presence of an aliphatic hydrocarbon solvent or a chlorinated aliphatic hydrocarbon solvent as shown, for example, by a paper by Takeshi Nishiguchi and Fumi Asano entitled "Oxidation of Alcohols by Metallic Nitrates Supported on Silica Gel" (J. Org. Chem. 1989, 54, 1531-1535).

Barak et al., in a paper entitled "Selective Oxidation of Alcohols by a H$_2$O$_2$-RuCl$_3$ System under Phase-Transfer Conditions" (J. Org. Chem., 1988, Vol. 43, pp. 3553-3555), discloses in part that secondary alcohols can be oxidized to ketones with one hundred percent selectivity when using hydrogen peroxide as the oxidizing agent.

A paper entitled "Fast and Selective Oxidation of Primary Alcohols to Aldehydes or to Carboxylic Acids and of Secondary Alcohols to Ketones Mediated by Oxoammonium Salts under Two-Phase Conditions" by Anelli et al. (J. Org. Chem., 1987, Vol. 52, pp. 2559-2562) discloses oxidation of a variety of alcohols in solution in methylene chloride with sodium hypochlorite.

In copending Sanderson et al., U.S. application Ser. No. 07/444211, filed Dec. 1, 1989, and entitled "Ketone Derivatives of Polyoxypropylene Glycols", now U.S. Pat. No. 4,980,514, a process is disclosed wherein diketones are prepared by the oxidation of a polyoxypropylene glycol with an alkali metal or alkaline earth metal hypochlorite in the presence of a halogenated alkane solvent and a ruthenium catalyst.

In copending Sanderson et al., U.S. application Ser. No. 07/448428, filed Dec. 1, 1989, and entitled "Oxidation of Polyoxypropylene Glycols", now U.S. Pat. No. 4,978,785, a process is disclosed wherein carboxylic acid derivatives and methyl ketone derivatives of polyoxypropylene glycols are prepared by controlled nitric acid oxidation.

U.S. Pat. No. 4,141,919 discloses a process for producing alkoxy ketones by dehydrogenating an alkoxyalkanol in the presence of pre-activated copper-containing catalyst.

SUMMARY OF THE INVENTION

This invention relates to ketone-terminated polyoxyalkylene compounds of the formula:

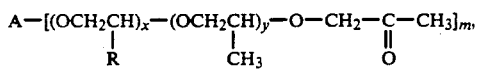

wherein:

A is linear or branched alkyl of 1 to about 18 carbon atoms and, preferably, 1 to about 12 carbon atoms as exemplified by methyl, ethyl, isopropyl, t-butyl, hexyl, octyl, lauryl, etc., or represents the nucleus of an oxyalkylation susceptible trifunctional polyhydric compound having 3 to about 20 carbon atoms and, preferably, 3 to about 10 carbon atoms as exemplified by glycerine, trimethylolpropane, etc., or is the radical

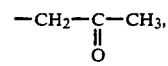

R is hydrogen or the methyl or ethyl radical, x ranges from 0 to about 20, y ranges from 1 to about 50, m is 1 or 3 with the proviso that when A is alkyl or the said radical m is 1 and when A is the said nucleus M is 3.

The polyoxyalkylene ketone compounds of this invention are prepared, for example, by initially adding predetermined amounts of glacial acetic acid, a hydroxyl-terminated polyoxyalkylene compound such as a polyoxypropylene glycol and, optionally, water, to a reaction zone and by continuously adding an aqueous solution of an alkali metal or an alkaline earth metal hypochlorite oxidant to the reaction zone with agitation under reaction conditions including a temperature of about 10° to about 50° C., a pressure of about 0 to 1,000 psig, and a total reaction time of about 0.5 to 20 hours, whereby the hydroxyl-terminated compound will be substantially selectively converted to the corresponding ketone-terminated compound, and recovering the said ketone, the glacial acetic acid being added in the ratio of about 5 to about 500 parts by weight of glacial acetic acid per 100 parts by weight of said hydroxyl-terminated polyoxyalkylene compound, the water, when added, being added in the ratio of about 5 to about 100 parts by weight of water per 100 parts of the hydroxyl-terminated polyoxyalkylene compound and in the ratio of about 1 to about 3 parts of water per part of glacial acetic acid.

the aqueous solution of the hypochlorite containing from about 5 to about 25 wt. % of the alkali metal or alkaline earth metal hypochlorite and being slowly added to the reaction zone over a period of time of about 0.5 to 5 hours in an amount within the range from about 10 to about 100 parts by weight of the hypochlorite per 100 parts by weight of the hydroxyl-terminated polyoxyalkylene compound.

In accordance with another embodiment of the process employed to prepare the ketone compounds of this invention, wherein only a catalytically effective amount of glacial acetic acid is used, hydroxyl-terminated polyoxyalkylene compound, such as a polyoxypropylene glycol, and about 5 to about 100 parts by weight of glacial acetic acid per 100 parts by weight of polyoxypropylene glycol, are initially added to the reaction zone and the aqueous solution of alkali metal or alkaline earth metal hypochlorite oxidant is thereafter added to the reaction zone with agitation under the reaction conditions recited above to substantially selectively convert the hydroxyl-terminated polyoxyalkylene compound to the corresponding ketone, and the ketone is thereafter recovered from the reaction product.

In accordance with still another embodiment of the process employed to prepare the polyoxyalkylene ketones of the present invention, wherein a catalytically effective amount of glacial acetic acid is used and wherein a minor amount of water is added to the reaction zone to enhance the catalytic effectiveness of the glacial acetic acid, the hydroxyl-terminated polyoxyalkylene compound, such as a polyoxypropylene glycol, and about 5 to about 100 parts by weight of glacial acetic acid per 100 parts by weight of the polyoxyalkylene compound, together with about 5 to about 100 parts by weight of water per 100 parts by weight of the polyoxyalkylene compound and in the ratio of about 1 to about 3 parts of water per part of glacial acetic acid, are initially added to the reaction zone and the aqueous solution of alkali metal or alkaline earth metal hypochlorite oxidant is thereafter added to the reaction zone with agitation under the reaction conditions recited above to substantially selectively convert the polyoxyalkylene compound to the corresponding ketone, and the ketone is thereafter recovered from the reaction product.

The method of preparing the ketone-terminated polyoxyalkylene compounds of this invention is more completely described in copending Sanderson et al., U.S. application Ser. No. 07/456,891, filed Dec. 26, 1989 and entitled "Manufacture of Ketone Derivatives of Polyoxypropylene Glycols", now U.S. Pat. No. 4,960,948, which is incorporated herein in its entirety by reference.

DESCRIPTION OF THE PREFERRED EMBODIMENTS

The starting materials for preparing the ketone compounds of the present invention include hydroxyl-terminated polyoxyalkylene compounds such as polyoxypropylene glycols, glacial acetic acid, an alkali metal or alkaline earth metal hypochlorite and, optionally, a minor amount of water.

A polyoxypropylene glycol feedstock especially useful for preparing the polyoxyalkylene diketones of the present invention is a polyoxypropylene glycol having the formula:

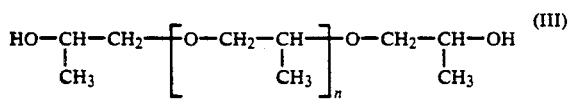

(III)

wherein n is a positive integer having a value of 1 to about 50.

The polyoxypropylene glycol feedstocks are prepared commercially by reacting an initiator such as propylene glycol with an amount of propylene oxide sufficient to provide a polyoxypropylene glycol of the desired molecular weight. Since the addition of the propylene oxide is random, the final propoxylation product will not be a pure compound but, rather, will be a mixture of polyoxypropylene glycols. For example, if the amount of propylene oxide that is used is adequate to provide for a polyoxypropylene glycol having an average molecular weight of about 1,000, the final propoxylation product will actually be composed of a mixture of polyoxypropylene glycols having molecular weights varying from about 800 to about 1,200, the molecular weight distribution following a Gaussian distribution curve (sometimes referred to as a sine curve or a Poissan curve). As the average molecular weight of the polyoxypropylene glycol increases, the spread in molecular weight will also increase. Thus, when the average molecular weight of the polyoxypropylene glycol is 3,000, the deviation will be about 400 molecular weight units so that most of the product will fall within the molecular weight range of about 2,600 to about 3,400.

Also, the final propoxylation product will contain a minor amount of impurities (normally 5 wt. % or less) resulting, for example, from dehydration of terminal hydroxypropyl end groups which can occur to a limited extent at the reaction temperatures used during the propoxylation. A small portion of the feedstock will contain hydroxyethyl end groups.

Representative products of this nature include, for example, a polyoxypropylene glycol manufactured and sold by Texaco Chemical Company having an average molecular weight of about 230 (PPG-230), a polyoxypropylene glycol having an average molecular weight of about 400 (PPG-400) sold by the Texaco Chemical Company and a polyoxypropylene glycol having an average molecular weight of about 2,000 (PPG-2000) sold by the Texaco Chemical Company.

Trifunctional polyoxyalkylene compounds useful in making the polyoxyalkylene ketones of this invention include, for example, compounds of the formula:

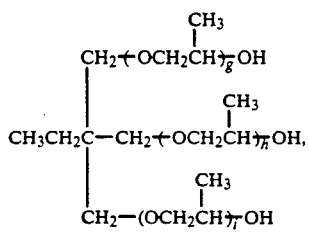

wherein the sum of $g+h+i$ is about 5.3 and of the formula:

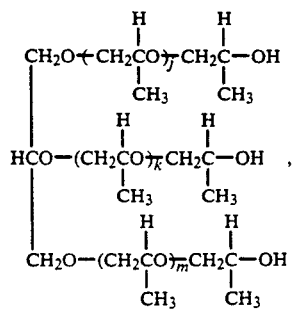

wherein the sum of $j+k+m$ is about 85.

Monofunctional polyoxyalkylene compounds useful in preparing the ketone-terminated polyoxyalkylene compounds of this invention include, for example, compounds of the formula:

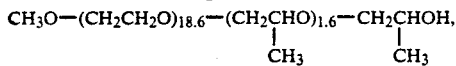

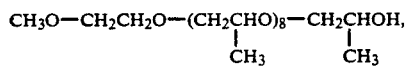

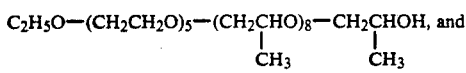

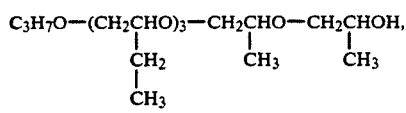

Both the monofunctional as well as the trifunctional polyoxyalkylene compounds referred to above can be conveniently prepared by methods well known in the art by reacting the appropriate initiator with an alkylene oxide or oxides in the presence of a suitable catalyst such as potassium hydroxide.

It is important to use glacial acetic acid in preparing the ketone products of the present invention. Glacial acetic acid functions both as a solvent and as a catalyst. A controlled amount of water, within the range of about 1 to 3 parts of water per part of glacial acetic acid can be used to enhance the catalytic activity of the glacial acetic acid, but the use of larger amounts of water is deleterious.

The oxidant to be used in accordance with the present invention is an alkali metal or akaline earth metal hypochlorite such as sodium hypochlorite, calcium hypochlorite, potassium hypochlorite, etc.

The Reaction Procedure

The reaction procedure to be used in preparing the ketone-terminated polyoxyalkylene compounds of the present invention is a procedure wherein the hydroxyl-terminated polyoxyalkylene compound, such as, for example, a polyoxypropylene glycol, glacial acetic acid and water, if any, are added to a suitable reaction vessel, such as an autoclave, provided with appropriate agitation means and means for controlling temperature within the autoclave such as a jacket through which a heat exchange fluid may be circulated.

The hypochlorite oxidant is preferably employed in the form of 5 to 25 wt. % aqueous solution of the hypochlorite.

In the process utilized in producing the products of the present invention, the hydroxyl-terminated polyoxyalkylene starting material, glacial acetic acid, and water, if any, are initially added to a reaction zone and thereafter the aqueous solution of alkali metal or alkaline earth metal hypochlorite oxidant is slowly added to the reaction zone with agitation.

The reaction conditions to be employed include a temperature of about 10° to about 50° C. (and more preferably about 10° to about 30° C.), a pressure of about 0 to 1,000 psig. (preferably autogenous pressure) and a reaction time of about 0.5 to 20 hours, and more preferably, about 0.5 to about 5 hours.

The oxidation reaction will be substantially complete at the end of the hypochlorite addition period, which will normally require from about 2 to about 5 hours, but since the oxidation reaction is a second order reaction, it will normally require about 15 to 20 hours of reaction at the indicated reaction temperature in order to bring the oxidation reaction to completion.

In general, the glacial acetic acid should be added to the reaction zone in the ratio of about 5 to about 500 parts by weight of glacial acetic acid per 100 parts by weight of the hydroxyl-terminated polyoxyalkylene compound glycol.

When the glacial acetic acid is to be used primarily as a solvent, it should be added to the reaction zone in the ratio of about 100 to about 500 parts by weight of glacial acetic acid per 100 parts by weight of said hydroxyl-terminated starting material, and more preferably in the ratio of about 200 to about 300 parts by weight of glacial acetic acid per 100 parts by weight of said hydroxyl-terminated starting material.

When the glacial acetic acid is to be used primarily as a catalyst, it should be added to the reaction zone in the ratio of about 5 to about 100 parts by weight of glacial acetic acid per 100 parts by weight of the said hydroxyl-terminated starting material.

When water is to be added to enhance the catalytic activity of the glacial acetic acid, the water should be added in the ratio of about 5 to about 100 parts by weight of water per 100 parts of hydroxyl-terminated starting material and in the ratio of about 1 to about 3 parts of water per part of glacial acetic acid.

The aqueous solution of alkali metal or alkaline earth metal hypochlorite should preferably contain from about 5 to about 25 wt. % of hypochlorite and the amount of aqueous solution of the hypochlorite slowly added to said reaction zone should be an amount such that from about 10 to about 100 parts of hypochlorite is added to the reaction zone per 100 parts by weight of said hydroxyl-terminated starting material, and more preferably in the ratio of about 20 to about 50 parts by weight of hypochlorite per 100 parts of At the end of the reaction, the polyoxypropylene ketone may be recovered from the reaction mixture in any suitable manner, such as by solvent extraction (e.g., solvent extraction with a chlorinated alkane such as trichlorethane, as shown in the examples, by extractive distillation, etc.

As a result, the hydroxyl-terminated feedstock will be substantially selectively converted to the corresponding ketone derivative.

As indicated, when the feedstock employed is a polyoxypropylene feedstock, it will comprise a mixture of polyoxypropylene glycols and minor amounts of other impurities. Thus, for example, although 95 wt. % or more of the polyoxypropylene glycol feedstock will contain terminal hydroxypropyl end groups that are substantially selectively oxidized to ketone end groups when using the process of the present invention, the feedstock will contain a small amount of feed components having terminal hydroxyethyl end groups. The hydroxyethyl end groups will normally be oxidized to carboxylic acid groups.

Also, the methylene group adjacent an ether group is susceptible to limited oxidation, i.e.,

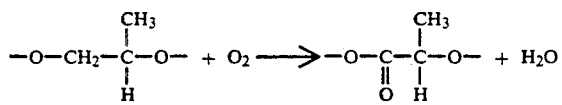

The invention is further illustrated by the following specific examples which are given by way of illustration and not intended to be limitative.

EXAMPLE 1

Preparation of the Diketone of Polypropylene Glycol-1000 (6528-3)

In this example glacial acetic acid was utilized as a solvent.

Polypropylene glycol-2000 (50g, Hydroxyl No. 55.7), and acetic acid (150 g) were charged to a 500 ml flask equipped with stirrer, water bath, thermometer, condenser and addition funnel. Sodium hypochlorite (74 g, 10%) was added dropwise over 0.5 hour. There was a mild exotherm but the temperature was maintained at 20°-25° C. by means of a water/ice bath. The reaction mixture was stirred for an additional 15 hours at 20°-25° C. The mixture was then poured into 500 ml water and the polyol extracted with 1,1,1-trichloroethane (3×100 ml). The trichloroethane was extracted (3×50 ml) with 5% $NaHCO_3$ (1×50 ml)water. The organic solution was then dried over sodium sulfate. The solvent was removed on a rotary evaporator to give 45. g of the diketone products, a clear liquid which had the following analytical results:
Hydroxyl No=42.6 mg KOH/g
Acid No.=1.76 mg KOH/g
Water=0.140 wt. %

EXAMPLE 2

Preparation of the Diketone of Polypropylene Glycol-2000 (6528-4)

Polypropylene glycol-2000 (200g, Hydroxyl No. 55.7), and acetic acid (400 g) were charged to a 100 ml flask equipped with stirrer, water bath, thermometer, condenser, and addition funnel. 10% sodium hypochlorite (600 g) was added dropwise over about 1 hour. There was a mild exotherm but the temperature was maintained at °°-25° C. by means of a water bath. The reaction mixture was stirred for an additional 15 hours at 20°-25° C. The mixture was then poured into 100 ml water and the polyol extracted with 1,1,1-trichloroethane (3×200 ml). The trichlorethane solution was extracted (3×100 ml) with 5% $NaHCO_3$. The organic solution was then dried rotary evaporator (water bath 80° C., water aspirator), 186.1 g of the diketone product, a clear, light-yellow liquid, was obtained which had the following analytical results:
Hydroxyl No.=12.6 mg KOH/g
Acid No.=27.4 mg KOH/g (due to acetic acid remaining)
Water=0.059 wt. %

EXAMPLE 3 (COMPARISON)

Oxidation of Polypropylene Glycol (6495-4)-2000 with NaOCl (D-6495-4)

Polypropylene glycol-2000 (100 g; Hydroxyl No. 55.7) was charged to a 100 ml flask with 100 ml water and 400 g 10% NaOCl. The mixture was heated slowly to 90°-100° C. and held at 92° C. for 5 hours. The reaction mixture was cooled to ambient temperature, 50 g conc. HCl added and the polyol extracted with methylene chloride (3×200 ml). The organic layer was washed with water (3×100 ml) and then dried over anhydrous $Na_2SO_4$. The solvent was removed on a rotary evaporator to give 95.2 g of clear, light yellow oil. The following analytical results were obtained.
Hydroxyl No.=77.6 mg KOH/g
Acid No.=11.4 mg KOH/g
Water=0.013 wt. %
Carbonyl (by titration)=<0.02%

EXAMPLES 4-11

Preparation of the Diketone by Polypropylene-2000

When the glacial acetic acid is used primarily as a catalyst, and only secondarily as a solvent, a higher conversion of the polyoxypropylene glycol is obtainable. This is illustrated by the examples that are summarized in Table I. Each of the examples of Table I was conducted in the manner described above for Example 1.

TABLE I

OXIDATION OF POLYOXYPROPYLENE GLYCOLS USING CATALYTIC QUANTITIES OF GLACIAL ACETIC ACID

| Example Number | PPG-[a] 2000 (g) | 10%[b] NaOCl (g) | HOAC[c] (g) | Time NaOCl Addn. (Hr.) | Reaction[d] Time (Hr.) | Temp. (°C.) | Hydroxyl No. mg KOH/g | Acid No. mg KOH/g | Water (wt. %) |
|---|---|---|---|---|---|---|---|---|---|
| 4 (6528-3) | 50 | 74 | 150 | 0.5 | 15 | 20-25 | 42.6 | 1.76 | 0.140 |
| 5 (6528-5) | 50 | 74 | 60 | 0.5 | 1 | 20-25 | 30.9 | 2.43 | 0.061 |
| 6 (6528-6) | 50 | 74 | 30 | 0.5 | 2 | 20-25 | 17.3 | 1.23 | 0.024 |
| 7 (6528-7) | 50 | 74 | 6 | 0.5 | 0.5 | 20-25 | 32.6 | 1.47 | 0.051 |
| 8 (6528-9) | 50 | 100 | 5 | 1 | 0.5 | 20-25 | 16.4 | 5.65 | 0.022 |
| 9 (6528-18) | 100 | 250 | 33 | 0.5 | 1 | 20-25 | 20.8 | 2.16 | 0.096 |
| 10 (6528-19) | 100 | 250 | 20 | 1 | 2.2 | 20-25 | 14.3 | 1.89 | 0.158 |
| 11 | 100 | 250 | 40 | 1 | 1 | 20-25 | 23.0 | 2.48 | 0.016 |

TABLE I-continued
OXIDATION OF POLYOXYPROPYLENE GLYCOLS USING CATALYTIC QUANTITIES OF GLACIAL ACETIC ACID

| Example Number | PPG-$^a$ 2000 (g) | 10%$^b$ NaOCl (g) | HOAC$^c$ (g) | Time NaOCl Addn. (Hr.) | Reaction$^d$ Time (Hr.) | Temp. (°C.) | Hydroxyl No. mg KOH/g | Acid No. mg KOH/g | Water (wt. %) |
| --- | --- | --- | --- | --- | --- | --- | --- | --- | --- |
| (6528-20) | | | | | | | | | |

$^a$Polypropylene glycol-2000 with Hydroxyl No. 55.7.
$^b$10% NaOCl sold as swimming pool bleach.
$^c$Glacial acetic acid 99%.
$^d$Reaction time from end of NaOCl addition to workup.

Note from the results reported in Table I that as the amount of glacial acetic acid was progressively decreased in Examples 4-8, there was a reduction in the hydroxyl number of the product and also a reduction in the acid number of the product. The decrease in hydroxyl number indicates that the conversion of the polyoxypropylene was increased and the decrease in the acid number indicates that there was improved selectivity to the ketone product, rather than to a carboxylic acid derivative.

A similar effect is noted in comparing Example 11 with Examples 9 and 10.

EXAMPLE 12

Preparation of the Diketone of Polypropylene Glycol-1000 (6528-93)

Polypropylene glycol-1000 (PPG-1000, a product having an average molecular weight of about 1000 made by the Texaco Chemical Company, Houston, Texas) (1000 g., Hydroxyl No. 106-107), acetic acid (200 g) and demineralized water (400 g) were charged to a three-neck flask equipped with stirrer, water bath, thermometer, condenser and large addition funnel. Sodium hypochlorite (2000 g, 10%) was added to the stirred solution over 2-2.5 hours. The temperature was maintained at 25° C. by the addition of ice to the water bath. The reaction mixture was stirred for an additional 15 hours at 25° C. Cyclohexane (1000 ml) was poured into the flask resulting in the formation of two layers with the upper layer being the organic phase and the lower layer being the aqueous phase. The organic and the aqueous layers were separated and the aqueous layer extracted 2×200 ml cyclohexane. The combined organic layers where then extracted (1×200 ml H$_2$O) (2×200 ml 5% NaHCO$_3$), and dried over anhydrous Na$_2$SO$_4$. The cyclohexane was removed on a rotary evaporator to give 961 g of the diketone product, a pale yellow to clear oil.

Analysis of the product gave the following results:
Hydroxyl No. 22.5 mg KOH/g
Acid No. 2.47 mg KOH/g
Saponification Value 8.02 mg KOH/g
IR analysis indicated the presence of ketone carbonyl.

EXAMPLE 13

Preparation of the Diketone of Polypropylene Glycol-2000 (6528-94)

The procedure and work-up followed in this example were the same as in Example 12 except that polypropylene-2000 (PPG-2000, Hydroxyl No. 56-57, a product having an average molecular weight of about 2000 made by the Texaco Chemical Company, Houston, Tex.) was charged to the reaction flask. After solvent removal 946 g of the diketone product, a light yellow oil, was obtained.

Analysis of the product gave the following results:
Hydroxyl No. 8.19 mg KOH/g
Saponification Value 15.4 mg KOH/g
IR analysis indicated the presence of ketone carbonyl.

EXAMPLE 14

Preparation of the Monoketone of an Ethoxylated-Propoxylated C$_{10-12}$ Mixed Alcohol (6528-95)

The procedure followed in this example was the same as in Example 12 except that 825 g of a special alcohol adduct was added. This monofunctional product which was prepared from a C$_{10-12}$ mixed alcohol ethoxylated to an average degree of 2 ethylene oxide groups followed by propoxylation to an average of 6 propylene oxide groups had a molecular weight of about 600. After solvent removal, 806 g of the monoketone product was obtained.

Analysis of the product gave the following results:
Hydroxyl No. 22.7 mg KOH/g
Acid No. 2.02 mg KOH/g
Saponification Value ~0
IR analysis indicated the presence of ketone carbonyl.

What is claimed is:

1. A compound of the formula:

$$A[-(OCH_2CH)_x-(CH_2CH)_y-O-CH_2-\underset{\underset{O}{\|}}{C}-CH_3]_m$$
$$\phantom{A[-(OC}|\phantom{H_2CH)_x-(CH_2C}|$$
$$\phantom{A[-(OCH}R\phantom{H)_x-(}CH_3$$

wherein:
A is linear or branched alkyl of 1 to about 18 carbon atoms or represents the nucleus of a 3 to 20 carbon atom oxyalkylation susceptible acyclic triol or is the radical $$-CH_2-\underset{\underset{O}{\|}}{C}-CH_3,$$

R is hydrogen or the methyl or ethyl radical,
x ranges from 0 to about 20,
y ranges from 1 to about 50,
m is 1 or 3 and with the proviso that when A is alkyl or the said radical m is 1 and when A represents the said nucleus m is 3.

2. The compound of claim 1 wherein A is alkyl of from 1 to about 18 carbon atoms.

3. The compound of claim 1 wherein A is the said nucleus of the oxyalkylation susceptible acyclic triol.

4. The compound of claim 1 wherein A is the radical

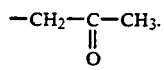

5. The compound of claim 1 wherein R is hydrogen.
6. The compound of claim 1 wherein A is methyl.
7. The compound of claim 1 wherein A represents the nucleus of a 3 to 6 carbon atom oxyalkylation susceptible acyclic triol.
8. The compound of claim 3 wherein the said oxyalkylation susceptible acyclic triol is glycerine.
9. The compound of claim 3 wherein the said oxyalkylation susceptible acyclic triol is glycerine and x is 0.
10. The compound of claim 1 wherein A represents a trimethylolpropane nucleus.
11. The compound of claim 1 wherein A represents a trimethylolpropane nucleus and x is 0.
12. The compound of claim 1 wherein A is alkyl of from 1 to 18 carbon atoms and R is hydrogen.
13. The compound of claim 1 wherein A is methyl and R is hydrogen.
14. The compound of claim 1 wherein A is the radical

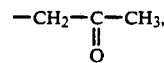

and x is 0.

* * * * *